United States Patent [19]

Fringeli

[11] 4,024,071

[45] May 17, 1977

[54] 4,4'-BIS-(s-TRIAZIN-6-yl-AMINO)-STILBENE-2,2'-DISULPHONIC ACID

[75] Inventor: Werner Fringeli, Basel, Switzerland

[73] Assignee: Ciba-Geigy Corporation, Ardlsey, N.Y.

[22] Filed: Jan. 7, 1976

[21] Appl. No.: 647,243

[30] Foreign Application Priority Data

Jan. 22, 1975 Switzerland .......................... 770/70

[52] U.S. Cl. .......................... 252/301.23; 162/162; 260/240 B; 427/158
[51] Int. Cl.$^2$ ...................................... C07D 403/00
[58] Field of Search ........... 260/240 B; 252/301.23; 162/162

[56] References Cited

UNITED STATES PATENTS 3,766,083  10/1973  Langstroth et al. ............ 260/240 B

FOREIGN PATENTS OR APPLICATIONS

| 379,513 | 8/1964 | Switzerland | 260/240 B |
| 1,287,581 | 8/1972 | United Kingdom | 260/240 B |
| 896,533 | 5/1962 | United Kingdom | 260/240 B |

*Primary Examiner*—Arthur P. Demers
*Attorney, Agent, or Firm*—Karl F. Jorda; Edward McC. Roberts; Prabodh I. Almaula

[57] ABSTRACT

The 4,4'-bis-[2'',4''-bis-(diisopropanolamino)-s-triazin-6''-yl-amino]-stilbene-2,2'-disulphonic acid, its manufacture as well as its use as optical brightener for natural or synthetic polyamides and especially for paper is disclosed.

3 Claims, No Drawings

4,4'-BIS-(s-TRIAZIN-6-yl-AMINO)-STILBENE-2,2'-DISULPHONIC ACID

The present invention relates to 4,4'-bis-[2'',4'''-bis-(diisopropanolamino)-s-triazin-6''-yl-amino]-stilbene-2,2'-disulphonic acid and its salts, and to its manufacture and its use for the optical brightening of natural or synthetic polyamides, and of paper.

Bis-s-triazinylamino-stilbene-2,2'-disulphonic acid monosubstituted on the triazine radical by hydroxyalkylamino radicals, and their use for the optical brightening of polyamides and paper, are already known. Furthermore, bis-s-triazinyl-amino-stilbene-2,2'-disulphonic acids disubstituted at the triazine radical by hydroxyalkylamino radicals, and their use for the optical brightening of paper, are already known from British patent specification No. 896,533.

The subject of the present invention is now the compound of the formula

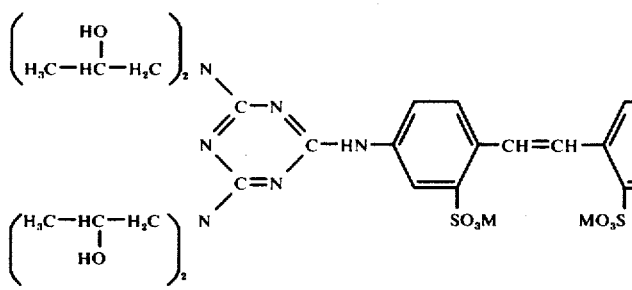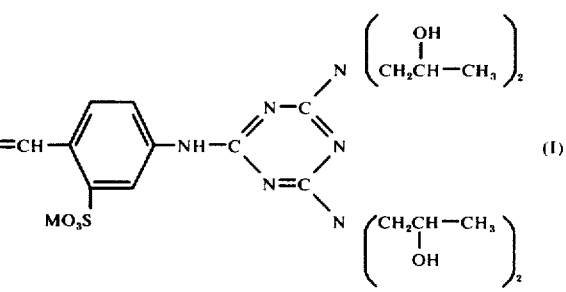

(I)

wherein M denotes a cation from the groups comprising hydrogen, alkali metal or unsubstituted or substituted ammonium, its manufacture, and its use for the optical brightening of natural or synthetic polyamides and especially of paper.

Preferred cations are the sodium or potassium ion or ammonium ions, such as, for example, those derived from ammonia or from nitrogen bases, such as monoalkylamines, dialkylamines and trialkylamines.

The compounds of the formula (I) are manufactured by reacting one mol of 4,4'-diaminostilbene-2,2'-disulphonic acid of the formula

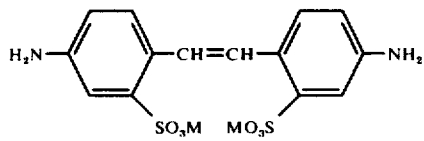

(II)

or its salts, in an aqueous medium and optionally in the presence of acid-binding agents, first with 2 mols of cyanuric chloride and then with 4 mols of the amine of the formula

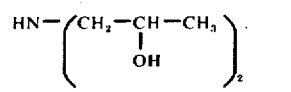

(III)

The first stage of the reaction is preferably carried out at temperatures below 10° C, the second stage at 0° to 30° C and the last stage at 50° to 100° C. Acid-binding agents which can be used for the first two stages of the reaction are above all alkali metal carbonates, bicarbonates, hydroxides or acetates, whilst in the third stage, in addition to alkali metal carbonates and hydroxides, as excess of base of the formula (III) is preferentially suitable. The reaction can be carried out both in a purely aqueous medium and also in a mixture of water and hydrophilic organic solvents which are inert towards the reactants. As such solvents it is above all possible to use low-molecular ketones, such as acetone or methyl ethyl ketone. The end product of the formula (I) is caused to separate out from its aqueous solutions by cooling these, or is isolated by salting-out, for example with alkali metal chlorides, or by evapoating the reaction solution to dryness. This last-mentioned method of isolation gives less pure product.

The salts of the new stilbene compound can be converted to the free sulphonic acid by treatment with strong mineral acids, such as, for example, 20% strength hydrochloric acid. The amine salts, which are mostly very readily water-soluble, can then be obtained from the free acid by neutralising with ammonia or with readily water-soluble primary, secondary or tertiary aliphatic or hydroaromatic amines. By subjecting the alkali metal salts of the new stilbene compound to a milder acid treatment, it is also possible to manufacture acid salts, which can equally be converted to very readily soluble products by neutralizing with low-molecular amines.

The new whitener, which in the form of its sodium or potassium salts is a colorless to pale yellowish-colored powder, is so readily soluble in water that it is possible to prepare liquid formulations of 10 to 25% strength, a state of affairs which is greatly valued by the users.

The new stilbene compound of the formula (I) is outstandingly suitable for brightening paper in combination with surface finishing, particularly by art coating.

The surface coating processes used for the surface finishing of paper are to be understood generally to include all operations which are concerned with finishing a raw paper by coating it with a finishing agent.

The surface finishing of paper is in practice generally carried out in accordance with the followng methods:

A. by so-called "starch sizing" in the paper machine, for example in a size press, or B. by so-called "pigment coating" within or outside the paper machine.

For starch coating (surface sizing according to A), aqueous sizing liquors are used, which generally contain, per liter, 0.1 to 8 g, for example 0.2 to 5 g, of optical brightener of the formula (I), 10 to 200 g of binder and optionally a small amount of customary wetting agent.

For pigment coating according to (B), coating liquors are generally used which per liter contain, for example, 0.1 to 8 g, preferably 0.2 to 5 g, of optical brightener of the formula (I), and, for example, 50 to 700 g, preferably 350 to 650 g, of white pigment and optionally, for example, 5 to 40%, preferably 8 to 30%, of binder, and, for example, 0.1 to 1%, preferably 0.2 to 0.6%, of metal-binding agents as well as, for example, 0.1 to 1%, preferably 0.2 to 0.6%, of wetting agents, these percentages being relative to the weight of the white pigment or pigments used.

The liquors usuable for starch coating and pigment coating can optionally also contain an aminoplast precondensate, by which there are to be understood addition products of formaldehyde with nitrogen compounds which can be methylolated.

The brightener of the formula (I) can also be used as a mixture with other brighteners in the liquors which are employed.

Possible binders are, for example, hydrolysed starch, alginates, polyvinyl alcohol, polyvinylpyrrolidone, carboxymethylcellulose, proteins (for example gelatine and casein), aqueous synthetic resin dispersions based on butadiene-styrene or acrylic polymers or copolymers, or mixtures of these binders.

A pigment coating which contains casein as the binder is also described as an art coating.

Examples of wetting agents are non-sulphated or sulphated higher alkanols or alkylphenol polyglycol ethers with an alkyl radical containing 8 to 14 carbon atoms and with 1 to 20 ethylene oxide groups.

Examples of white pigments which can be used are aluminium magnesium silicates (china clay), calcium carbonate, $CaSO_4 \cdot 10H_2O$ (satin white), Al silicates and hydroxides, barium sulphate (blanc fixe) or titanium dioxide or mixtures of such white pigments. In addition, the coating liquors can contain metal-binding agents, such as, for example, water-soluble polyphosphates or metaphosphates and polycarboxylic acid salts, for the purpose of eliminating undesired traces of metal (for example $Fe^{III}$).

In order to achieve good flow properties, it is advantageous to use an alkaline coating liquor for pigment coating. The alkaline reaction is suitably brought about by addition of ammonium hydroxide or sodium or potassium hydroxide, carbonate or borate, or their mixtures.

The coating of the paper with these coating liquors according to (A) and (B) is advantageously carried out in a coating apparatus customary for this purpose. This gives papers which in addition to having an improved surface and/or printability have a whiter and more attractive appearance.

In the surface finishing process, the paper is coated in the known manner, with aqueous brightener solutions being added to the ready-prepared sizing liquors or coating liquors.

As a rule, aqueous brightener solutions of 0.01 to 5% strength, preferably 0.05 to 2% strength, are used.

EXAMPLE 1

36.8 g of cyanuric chloride are dissolved in 150 g of acetone and introduced into 300 g of ice water, whilst stirring. A solution of 50.4 g of the sodium salt of 4,4'-diaminostilbene-2,2'-disulphonic acid in 360 g of water is allowed to run into the resulting cyanuric chloride suspension over the course of 45 minutes at $-5°$ to $+5°$ C, and the acid liberated is neutralised with a 15% strength sodium carbonate solution so that the pH value of the mixture remains at 3 to 4. Thereafter the mixture is stirred for a further hour at 0° to 5° C and a pH value of 4 to 5. 26.6 g of diisopropanolamine are now added to the reaction mixture, the pH value is kept at 7 to 8 with sodium carbonate solution and the mixture is stirred for 3 hours at 20° to 30° C. A further 28 g of diisopropanolamine are then added to the clear reaction solution and the reaction mixture is heated to $80°$ $-85°$ C for 3 hours whilst keeping the pH value at between 9 and 10 adding a 15% strength sodium hydroxide solution. The reaction mixture is cooled and the product which has separated out is filtered off and dried in vacuo at 80° C. 62 g of a yellow, water-soluble powder of the compound of the formula

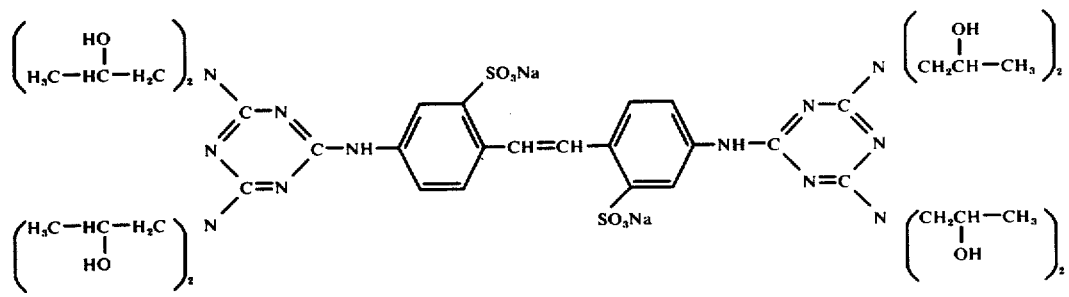

are obtained.

EXAMPLE 2

2 g of the optical brightener of the formula (I) are dissolved in 50 ml of distilled water at 90° C. Separately, 80 g of a hydrolysed starch are colloidally dissolved in 1,000 ml of water at 90° C. The brightener solution is then worked into the starch solution. The resulting solution can have a pH value of 5.5 to 7.

A sized printing paper is surface-coated with this sizing liquor in a size press and the coated paper is dried at about 90° to 120° C in the drier of the paper machine.

A paper of substantially improved whiteness is thus obtained.

Instead of sized paper, sized board can be used with equal success.

EXAMPLE 3

5 g of the optical brightener of the formula (I) are dissolved in 40 ml of distilled water at 90° C. 1,000 ml of an aqueous coating liquor which contains the following constituents are then added to this solution: 35 g of commercially available casein, 80 g of a synthetic resin dispersion, containing 50% of synthetic resin based on butadiene-styrene polymer (for example DOW- LATEX 626®, from Messrs. DOW Chemical, USA), 1 g of sodium polyphosphate, 2 g of sulphated dodecyl alcohol polyglycol ether with 15 ethylene oxide groups 400 g of aluminium magnesium silicate ("CHINA CLAY") and 15 g of concentrated ammonia.

The pH value of this dispersion is about 9.0. A sized paper or board is surface-coated with this coating liquor in the size press or other applicator devices.

An exceptionally white coated paper is obtained.

EXAMPLE 4

75 g of an anionic starch (for example Perfektamyl A 2177 17, AVEBE Holland) are stirred into 600 ml of cold water and are then colloidally dissolved at 80° to 90° C. 2 g of sodium polyphosphate, 2 g of sulphated dodecyl alcohol polyglycol ether with 15 ethylene oxide groups, 3 ml of concentrated ammonia, 75 g of a 50% strength synthetic resin dispersion based on a butadiene-styrene copolymer (for example DOW LATEX 636®, from Messrs. DOW CHEMICAL, USA), a solution of 0.5 g of the whitener of the formula (I) in 400 ml of water and, finally, 500 g of an aluminium magnesium silicate white pigment are added to this solution and the whole is stirred to give a homogeneous suspension.

A sized raw paper, consisting of 50% of bleached sulphite cellulose and 50% of mechanical wood pulp, and having a surface pH value of 4, is coated in a coating apparatus with the coating liquor described above. A very attractive white compression-proof paper is obtained which can be used, for example, in offset printing.

Higher contents of whitener, for example 2 or 8 g, also cause no undesired discoloration and instead produce a further increase in the white effect.

If, additionally, 4 g of polyvinyl alcohol are added as a blending agent for the whitener, to the coating liquor described above, the brightening effect is increased substantially.

EXAMPLE 5

A pigment coating liquor of the following composition is prepared: 150 ml of a 50% strength aqueous synthetic resin dispersion based on a crosslinkable methyl acrylate/methyl methacrylate/styrene copolymer (for example ACRONAL S 320 D® of Messrs. BASF in Ludwigshafen am Rhein, West Germany), 100 ml of water containing 2 g of sodium polyphosphate, 600 ml of water containing 4 g of the whitener of the formula (I), 50 ml of water containing 2 g of nonylphenol pentadecaglycol ether and 500 g of aluminum magnesium silicate (china clay Dinkie A).

A sized and loaded sulphite cellulose raw paper is coated with this treatment liquor and is subsequently dried. A brilliant white, compression-proof paper is obtained.

EXAMPLE 6

An art coating liquor of pH value 11 is obtained by bringing together 500 ml of water containing 1 g of the brightener of the formula (I), 35 g of casein, 12 ml of concentrated ammonia, 75 ml of water containing 7.5 g of sodium carbonate, 80 ml of a 50% strength synthetic resin dispersion based on a butadiene-styrene copolymer (for example DOW LATEX 636®), 50 ml of water containing 1 g of sodium polyphosphate, 300 g of aluminium magnesium silicate (china clay SPS), 250 g of 40% strength $CaSO_4 \cdot 1OH_2O$ (satin white) and 50 ml of water containing 2 g of sulphated dodecyl alcohol polyglycol ether with 10 to 20 ethylene oxide groups.

Sized paper or board is surface-coated with this coating liquor in the size press or in other applicator devices.

An exceptionally white coated paper is obtained.

EXAMPLE 7

1 g of the brightener of the formula (I) is dissolved in 1,000 ml of desalinated water. 3 ml of this solution are added to 100 ml of water which contain 0.06 g of a hydroxyethylated fatty alcohol with, for example, 20 mols of ethylene oxide (for example Tinegal NA®). The resulting aqueous brightener solution is warmed to 60° C. A polyamide fabric (polyamide 6) weighing 3 g is then introduced into the warm solution. The temperature is raised to 95°–97° C over the course of 10 to 15 minutes and is maintained thereat for 30 minutes. The fabric is then rinsed for 2 minutes in running cold water and is subsequently dried at 60° C.

The fabric treated in this way shows a marked brightening effect.

EXAMPLE 8

1 g of the brightener of the formula (I) is dissolved in 1,000 ml of desalinated water. 3 ml of this solution are added to 100 ml of water which contain 0.06 g of a hydroxyethylated fatty alcohol with, for example, 20 mols of ethylene oxide (for example Tinegal NA®) and 0.12 ml of 85% strength formic acid. The resulting aqueous brightener solution is warmed to 60° C. A polyamide fabric (polyamide 6 or 66) weighing 3 g is then introduced into the warm solution. The temperature is raised to 95°–97° C over the course of 10 to 15 minutes and is maintained thereat for 30 minutes. The fabric is then rinsed for 2 minutes in running cold water and is subsequently dried for 20 minutes at 60° C.

The fabric treated in this way shows a distinct brightening effect.

EXAMPLE 9

1 g of the brightener of the formula (I) is dissolved in 1,000 ml of desalinated water. 7.5 ml of this solution are added to 110 ml of water which contain 0.06 ml of 40% strength acetic acid, 0.36 g of a bleaching agent and 0.06 g of a hydroxyethylated fatty alcohol with 20 mols of ethylene oxide (for example Tinegal NA®).

The resulting aqueous brightener solution is warmed to 40° C. A woollen fabric weighing 3 g is then introduced into the solution. The temperature is raised to 60° C over the course of 10 to 15 minutes and is maintained thereat for 60 minutes. The fabric is then rinsed for 2 minutes in running cold water and is subsequently dried for 20 minutes at 60° C.

The fabric treated in this way shows a distinct brightening effect.

What we claim is:

1. The compound of the formula

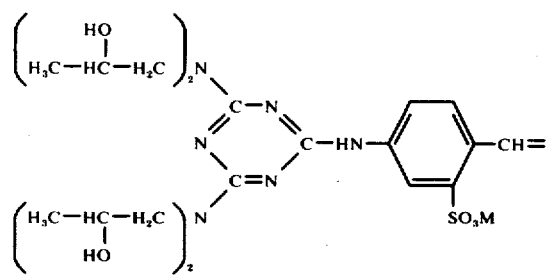 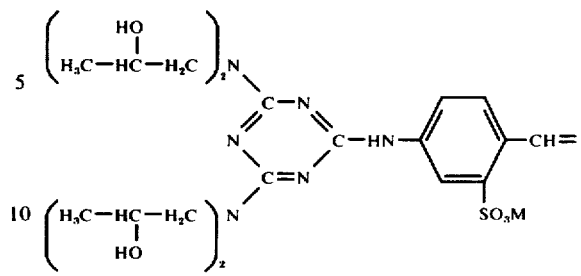

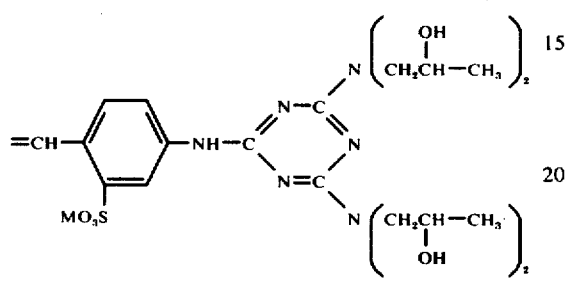 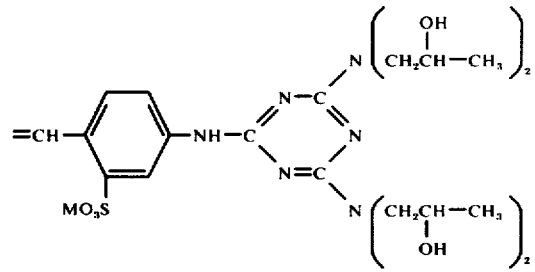

wherein M is a cation selected from the group consisting of hydrogen, alkali metal and unsubstituted or substituted ammonium.

2. In a process for the optical brightening of paper, which comprises incorporating into a coating composition for the surface treatment of paper the optical brightener compound of the formula wherein M is a cation selected from the group consisting of hydrogen, alkali metal and unsubstituted or substituted ammonium, and subsequently applying this coating composition to paper.

3. Process according to claim 2, wherein the optical brightener compound is incorporated into art coating compositions.

* * * * *